(12) United States Patent
Kimberley et al.

(10) Patent No.: US 6,472,341 B1
(45) Date of Patent: Oct. 29, 2002

(54) POLYMERIZATION CATALYSTS

(75) Inventors: Brian Stephen Kimberley, Sunbury on Thames; David Pratt, Egham, both of (GB)

(73) Assignee: BP Chemicals Limited, London (GB)

( * ) Notice: Subject to any disclaimer, the term of this patent is extended or adjusted under 35 U.S.C. 154(b) by 35 days.

(21) Appl. No.: 09/659,694

(22) Filed: Sep. 11, 2000

Related U.S. Application Data

(63) Continuation of application No. PCT/GB99/00716, filed on Mar. 10, 1999.

(30) Foreign Application Priority Data

| Mar. 12, 1998 | (GB) | ............................................. 9805336 |
| Mar. 20, 1998 | (GB) | ............................................. 9806106 |
| Mar. 27, 1998 | (GB) | ............................................. 9806661 |
| May 7, 1998 | (GB) | ............................................. 9809598 |
| Jul. 3, 1998 | (GB) | ............................................. 9814496 |
| Oct. 30, 1998 | (GB) | ............................................. 9823852 |

(51) Int. Cl.$^7$ .............................. B01J 31/18; C08F 4/44
(52) U.S. Cl. ....................... 502/155; 502/104; 502/167; 526/127; 526/161; 526/171; 526/172; 526/352
(58) Field of Search ................................ 526/127, 171, 526/161, 172, 75, 64; 502/104, 117, 152, 155, 168, 167

(56) References Cited

U.S. PATENT DOCUMENTS 5,955,555 A * 9/1999 Bennett ...................... 526/133

FOREIGN PATENT DOCUMENTS

WO WO 98/27124 6/1998

OTHER PUBLICATIONS

B.L. Small et al., "New Iron and Colbalt Catalysts for the Polymerization of Olefins", American Chemical Society Division of Polymer Chemistry, vol. 39, No. 1, p. 213, (1998).

G.J.P. Britovsek et al., "Novel Olefin Polymerization Catalysts Based on Iron and Cobalt", Chem. Commun., No. 7, pp. 849–850, (1998).

* cited by examiner

*Primary Examiner*—David W. Wu
*Assistant Examiner*—R. Harlan
(74) *Attorney, Agent, or Firm*—Finnegan, Henderson, Farabow, Garrett and Dunner, L.L.P.

(57) ABSTRACT

The present invention relates to transition metal based polymerization catalysts and their use in the polymerization and copolymerization of olefins.

32 Claims, 6 Drawing Sheets

Comparative Example 43

Comparative Example 26.1

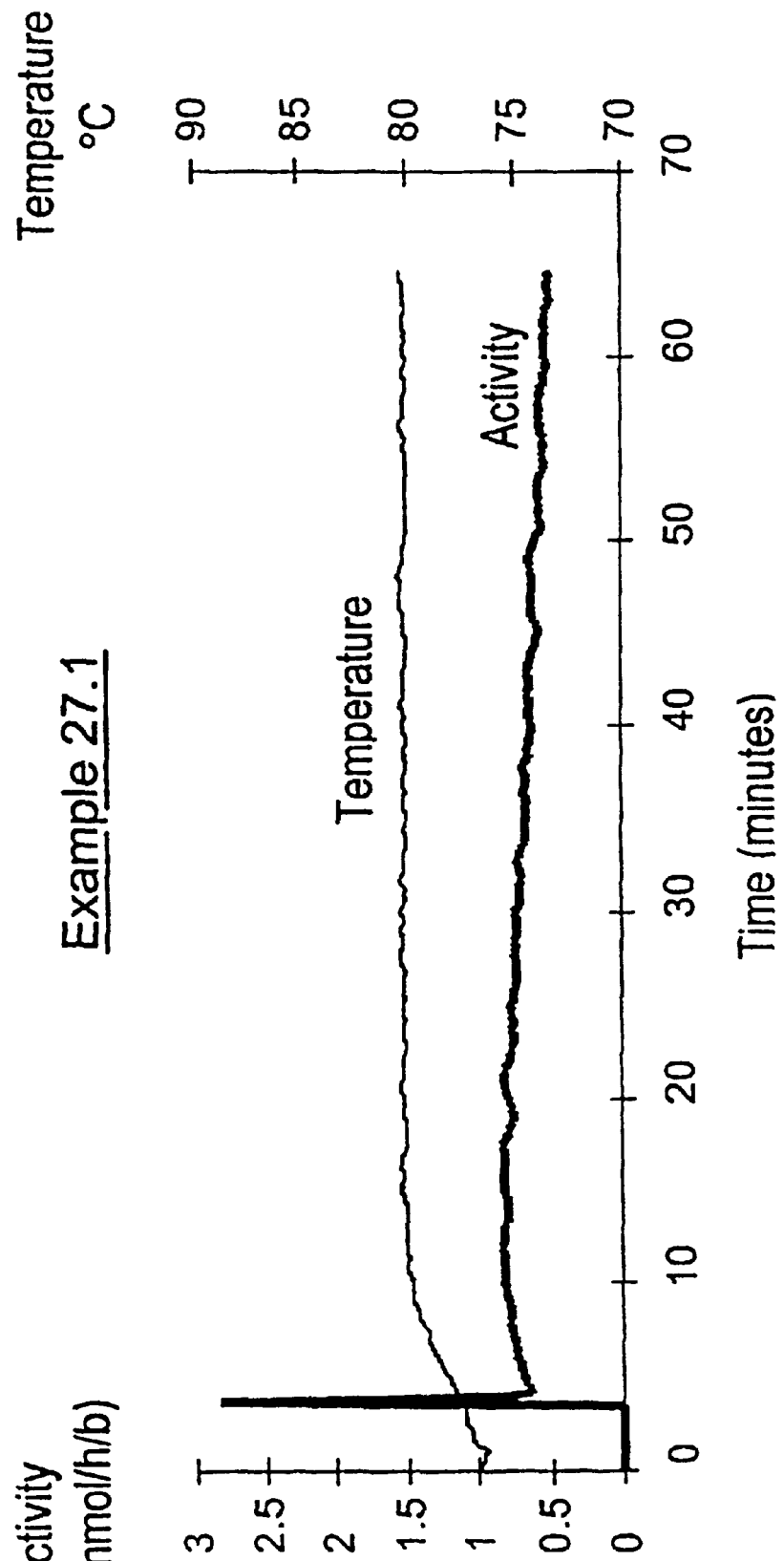

POLYMERIZATION CATALYSTS

Figure 1:
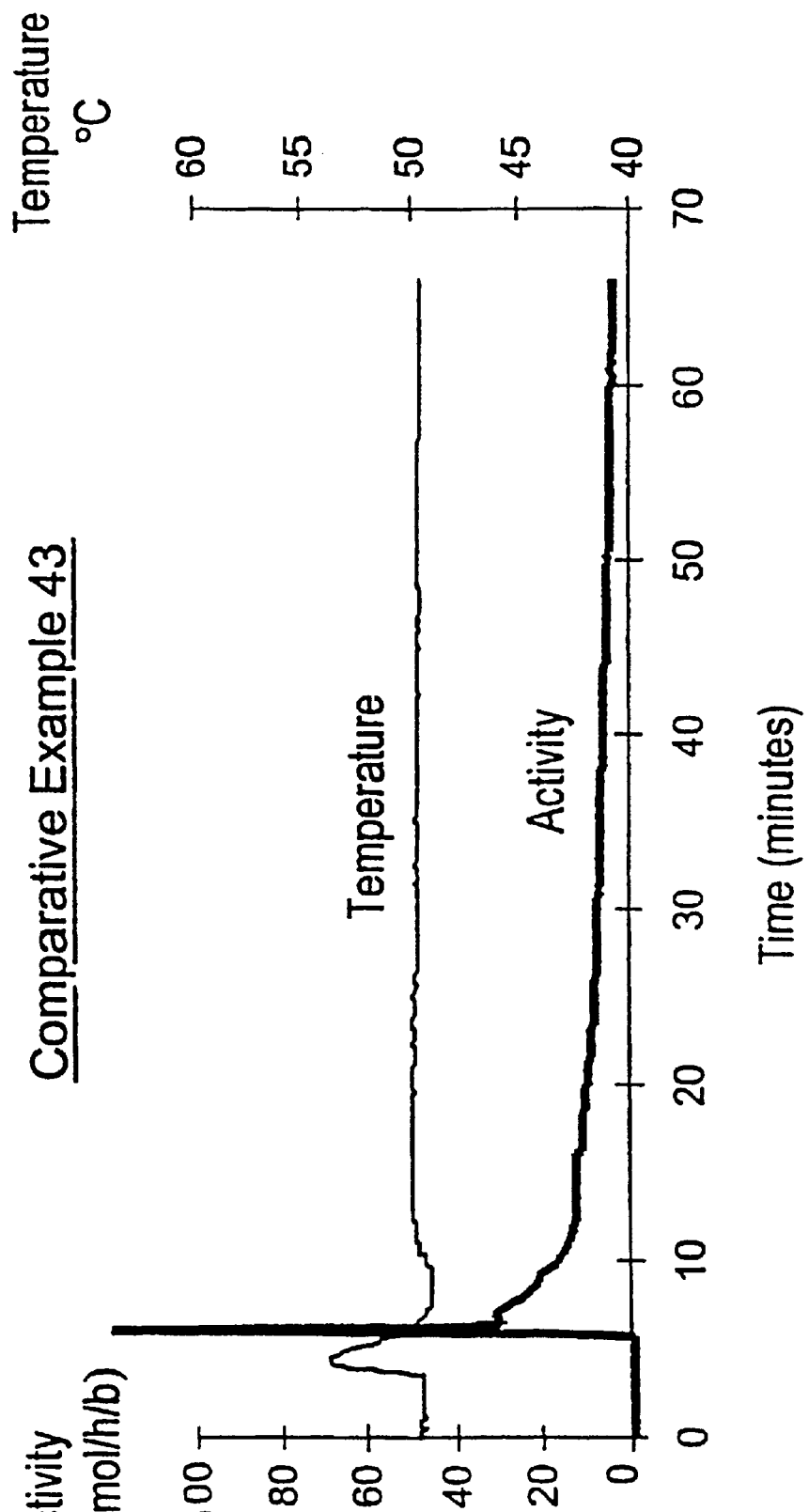

This application is a continuation of International Application No. PCT/GB99/00716 filed Mar. 10, 1999.

The present invention relates to transition metal based polymerisation catalysts and to their use in the polymerisation and copolymerisation of olefins.

The use of certain transition metal compounds to polymerise 1-olefins, for example, ethylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last twenty or thirty years, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10–50 bar) and low temperature (for example 50 to 150° C.).

Commodity polyethylenes are commercially produced in a variety of different types and grades. Homopolymerisation of ethylene with transition metal based catalysts leads to the production of so-called "high density" grades of polyethylene. These polymers have relatively high stiffness and are useful for making articles where inherent rigidity is required. Copolymerisation of ethylene with higher 1-olefins (eg butene, hexene or octene) is employed commercially to provide a wide variety of copolymers differing in density and in other important physical properties. Particularly important copolymers made by copolymerising ethylene with higher 1-olefins using transition metal based catalysts are the copolymers having a density in the range of 0.91 to 0.93. These copolymers which are generally referred to in the art as "linear low density polyethylene" are in many respects similar to the so called "low density" polyethylene produced by the high pressure free radical catalysed polymerisation of ethylene. Such polymers and copolymers are used extensively in the manufacture of flexible blown film.

In recent years the use of certain metallocene catalysts (for example biscyclopentadienylzirconiumdichloride activated with alumoxane) has provided catalysts with potentially high activity. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

Patent Application WO98/27124 published on Jun. 25, 1998 discloses that ethylene may be polymerised by contacting it with certain iron or cobalt complexes of selected 2,6-pyridinecarboxaldehydebis(imines) and 2,6-diacylpyridinebis(imines).

An object of the present invention is to provide a novel catalyst suitable for polymerising monomers, for example, olefins, and especially for polymerising ethylene alone or for copolymerising ethylene with higher 1-olefins. A further object of the invention is to provide an improved process for the polymerisation of olefins, especially of ethylene alone or the copolymerisation of ethylene with higher 1-olefins to provide homopolymers and copolymers having controllable molecular weights. For example, using the catalysts of the present invention there can be made a wide variety of polyolefins such as, for example, liquid polyolefins, oligomers, resinous or tacky polyolefins, solid polyolefins suitable for making flexible film and solid polyolefins having high stiffness.

The present invention provides a polymerisation catalyst comprising (1) a nitrogen-containing iron compound having the following Formula Z,

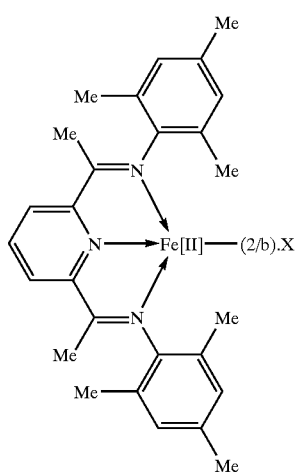

Formula Z and (2) an activating quantity of an activator compound selected from organoaluminium compounds and hydrocarbylboron compounds wherein X represents an atom or group covalently or ionically bonded to the Fe and b is the valency of the atom or group X, characterised in that the catalyst is supported on (3) a solid particulate support material.

Each of the nitrogen atoms in the compound of Formula Z is coordinated to the Fe atom by a "dative" bond, ie a bond formed by donation of a lone pair of electrons from the nitrogen atom. The remaining bonds on each nitrogen atom are covalent bonds formed by electron sharing between the nitrogen atoms and the organic ligand.

The atom or group represented by X in the compound of Formula Z is preferably selected from halide, sulphate, nitrate, thiolate, thiocarboxylate, $BF_4^-$, $PF_6^-$, hydride, hydrocarbyloxide, carboxylate, hydrocarbyl, substituted hydrocarbyl and heterohydrocarbyl. Examples of such atoms or groups are chloride, bromide, iodide, methyl, ethyl, propyl, butyl, octyl, decyl, phenyl, benzyl, methoxide, ethoxide, isopropoxide, tosylate, triflate, formate, acetate, phenoxide and benzoate.

Examples of the preferred atom or group X in the compounds of Formula Z are halide, for example, chloride, bromide; iodide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Most preferably X is selected from halide, hydride and hydrocarbyl. Chloride is particularly preferred.

The Formula Z compound is preferably 2,6-diacetylpyridinebis(2,4,6 trimethyl anil)FeCl$_2$.

The activator compound for the catalyst of the present invention is suitably selected from organoaluminium compounds and hydrocarbylboron compounds. Suitable organoaluminium compounds include trialkyaluminium compounds, for example, trimethylaluminium, triethylalumninium, tributylaluminium, tri-n-octylaluminium, ethylaluminium dichloride, diethylaluminium chloride and alumoxanes. Alumoxanes are well known in the art as typically the oligomeric compounds which can be prepared by the controlled addition of water to an alylaluminium compound, for example trimethylaluminium. Such compounds can be iinear, cyclic or mixtures thereof. Commercially available alumoxanes are generally believed to be mixtures of linear and cyclic compounds. The cyclic alumoxanes can be represented by the formula $[R^{16}AlO]_s$ and the linear alumoxanes by the formula $R^{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups.

Examples of suitable hydrocarbylboron compounds are dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)[(bis-3,5-trifluoromethyl)phenyl]borate$, trityltetra(pentafluorophenyl)borate and tris(pentafluorophenyl)boron.

In the preparation of the catalysts of the present invention the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per Fe atom in the compound of Formula Z.

The solid particulate support material employed in the present invention can be, for example, any organic or inorganic solid which does not deleteriously affect the catalyst properties. The support can be, for example, an inorganic oxide, hydroxide or salt, for example, silica, alumina, silica-alumina, zirconia, magnesia (magnesium oxide), magnesium chloride, pumice, talc, kieselguhr, calcium carbonate, calcium sulphate; or an organic polymer or prepolymer, for example polyethylene, polystyrene, or poly (aminostyrene). Preferred supports are silica, alumina, zirconia, talc, kieselguhr, or magnesia. Particularly preferred are, for example, silica, alumina, or zirconia, or a polymer or prepolymer, for example polyethylene or polystyrene.

The support material is preferably free from absorbed water or other materials which might deleteriously affect the performance of the catalyst of the present invention.

The particle size of the support material is suitable in the range 5 to 500 microns, preferably in the range 20 to 200 microns.

If desired the catalysts can be formed in situ in the presence of the support material, or the support material can be pre-impregnated or premixed, simultaneously or sequentially, with one or more of the catalyst components. If desired, the support material itself can be a heterogeneous catalyst, for example, a Ziegler Natta catalyst supported on a magnesium halide, a Phillips type (eg chromium oxide/silica) supported catalyst or a supported metallocene catalyst. Formation of the supported catalyst can be achieved for example by treating the compound of Formula Z with alumoxane in a suitable inert diluent, for example a volatile hydrocarbon, slurrying a particulate support material with the product and evaporating the volatile diluent. The produced supported catalyst is preferably in the form of a free-flowing powder.

The quantity of support material employed in the catalyst of the present invention can vary widely, for example from 100,000 to 1 grams per gram of Fe present in the Formula Z compound.

The surface area of the support material (BET) employed in the present invention is preferably in the range 5 to 1000 $m^2$ per gram, most preferably 50 to 500 $m^2$ per gram.

The catalyst can be supported on the support material in any suitable manner, for example using conventional impregnation techniques. For example, the catalyst components can be dissolved or suspended in a suitable diluent or solvent and slurried with the support material. The support material thus impregnated with catalyst can then be separated from the solvent or diluent, for example, by filtration or evaporation techniques. Alternatively the supported catalyst can be stored in the presence of liquid diluent or solvent if desired.

When it is desired to produce the supported catalyst in the form of an essentially dry powder, the latter suitably contains not more than 30 weight %, preferably not more than 10 weight %, most preferably not more than 1 weight % of liquid diluent.

A further aspect of the present invention provides a polymerisation catalyst system comprising (1) a compound having the Formula Z, (2) an activating quantity of an activator compound selected from organoaluminium and hydrocarbylboron compounds, wherein the catalyst is supported on (3) a solid particulate support material, and further comprising (4) a neutral Lewis base.

In this further aspect of the present invention the preferences in relation to the activator compound, the nature of the support material and other characteristics of the catalyst of the present invention are the same as expressed above. Neutral Lewis bases are well known in the art of Ziegler-Natta catalyst polymerisation technology. Examples of classes of neutral Lewis bases suitably employed in the present invention are unsaturated hydrocarbons, for example, alkenes (other than 1-olefins) or alkynes, primary, secondary and tertiary amines, amides, phosphoramides, phosphines, phosphites, ethers, thioethers, nitrites, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2), (3) and (4) of the catalyst system can be brought together simultaneously or in any desired order. However, if components (2) and (4) are compounds which interact together strongly, for example, form a stable compound together, it is preferred to bring together the components (1) and (2) in an initial step before adding component (4); or to bring together components (1) and (4) in an initial step before introducing component (2). The support material (3) can be introduced at any stage in the procedure. The quantities of components (1), (2) and (3) employed in the preparation of this catalyst system are suitably as described above. The quantity of the neutral Lewis Base [component (4)] is preferably such as to provide a ratio of component (1):component (4) in the range 100:1 to 1:1000, most preferably in the range 1:1 to 1:20. Components (1), (2), (3) and (4) of the catalyst system can brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating to higher temperatures e.g. up to 120° C. can be carried out if desired, e.g. to achieve better mixing of the components. It is preferred to carry out the bringing together of components (1), (2), (3) and (4) in an inert atmosphere (e.g. dry nitrogen) or in vacuo.

When it is desired to use a neutral Lewis base in the present invention, the supporting can be carried out, for example, by preforming the catalyst system comprising components (1), (2) and (4) and impregnating the support material preferably with a solution thereof, or by introducing to the support material one or more of the components simultaneously or sequentially. If desired the support material (3) itself can have the properties of a neutral Lewis base and can be employed as, or in place of, the optional component (4). An example of a support material having neutral Lewis base properties is poly(aminostyrene) or a copolymer of styrene and aminostyrene (ie vinylaniline).

The catalyst of the present invention can comprise, in addition to the compound of Formula Z, one or more other catalyst-forming transition metal compounds, for example one or more compounds having the general Formula B

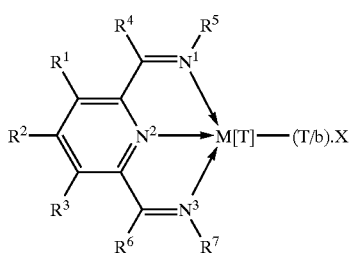

Formula B wherein
M is Fe[II], Fe[III], Co[I], Co[II], Co[III], Ru[II], Ru[III], Ru[IV], Mn[I], Mn[II], Mn[III] or Mn[IV]; X represents an atom or group covalently or ionically bonded to the transition metal M; T is the oxidation state of the transition metal M and b is the valency of the atom or group X; $R^1$, $R^2$, $R^3$, $R^4$, and $R^6$ are independently selected from hydrogen, halogen, hydrocarbyl, substituted hydrocarbyl, heterohydrocarbyl or substituted heterohydrocarbyl;
and such that (1):
when M is Fe, Co or Ru, $R^5$ and $R^7$ are independently selected from hydrogen, halogen, hydrocarbyl, substituted hydrocarbyl, heterohydrocarbyl or substituted heterohydrocarbyl; and when any two or more of $R^1$–$R^7$ are hydrocarbyl, substituted hydrocarbyl, heterohydrocarbyl or substituted heterohydrocarbyl, said two or more can be linked to form one or more cyclic substituents,
or such that (2):
when M is Fe, Co, Mn or Ru, then $R^5$ is represented by the group "P" and $R^7$ is represented by the group "Q" as follows:

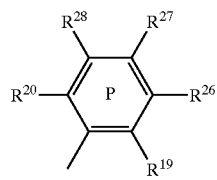 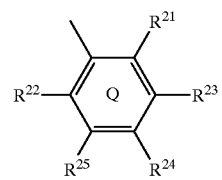

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of the ring systems P and Q forms part of a polyaromatic fused-ring system,
or such that (3)
when M is Fe, Co, Mn or Ru, then $R^5$ is a group having the formula —$NR^{29}R^{30}$ and $R^7$ is a group having the formula —$NR^{31}R^{32}$, wherein $R^{29}$ to $R^{32}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more can be linked to form one or more cyclic substituents; provided that said compound of Formula B is different from said compound of Formula Z.

Examples of suitable compounds of Formula B are 2,6-diacetylpyridinebis(2,6-diisopropylanil)FeCl$_2$
2,6-diacetylpyridine(2,6-diisopropylanil)MnCl$_2$
2,6-diacetylpyridine(2,6-diisopropylanil)CoCl$_2$
2,6-diacetylpyridinebis(2-tert.-butylanil)FeCl$_2$
2,6-diacetylpyridinebis(2,3-dimethylanil)FeCl$_2$
2,6-diacetylpyridinebis(2-methylanil)FeCl$_2$
2,6-diacetylpyridinebis(2,4-dimethylanil)FeCl$_2$
2,6-diacetylpyridinebis(2,6-dimethylanil)FeCl$_2$
2,6-dialdiminepyridinebis(2,6-dimethylanil)FeCl$_2$
2,6-dialdiminepyridinebis(2,6-diethylanil)FeCl$_2$
2,6-dialdiminepyridinebis(2,6-diisopropylanil)FeCl$_2$
2,6-dialdiminepyridinebis(1-naphthil)FeCl$_2$ and
2,6bis(1,1-diphenylhydrazone)pyridine.FeCl$_2$.

The catalysts of the present invention can also be employed in admixture with one or more other types of transition metal compounds or catalysts, for example, transition metal compounds of the type used in conventional Ziegler-Natta catalyst systems, metallocene-based catalysts, or heat activated supported chromium oxide catalysts (eg Phillips-type catalyst).

The present invention further provides a process for the polymerisation and copolymerisation of 1-olefins comprising contacting the monomeric olefin under polymerisation conditions with the polymerisation catalyst of the present invention.

Another embodiment of the present invention provides a process for the polymerisation and copolymerisation of 1-olefins comprising contacting the monomeric olefin under polymerisation conditions with the polymerisation catalyst of the present invention in the presence of hydrogen gas as a molecular weight modifier.

The polymerisation conditions can be, for example, solution phase, slurry phase or gas phase. If desired, the catalyst can be used to polymerise ethylene under high pressure/high temperature process conditions wherein the polymeric material forms as a melt in supercritical ethylene. Preferably the polymerisation is conducted under gas phase fluidised bed conditions.

Slurry phase polymerisation conditions or gas phase polymerisation conditions are particularly useful for the production. of high density grades of polyethylene. In these processes the polymerisation conditions can be batch, continuous or semi-continuous.

In the slurry phase polymerisation process the solid particles of supported catalyst are fed to a polymerisation zone either as dry powder or as a slurry in the polymerisation diluent. Preferably the particles are fed to a polymerisation zone as a suspension in the polymerisation diluent. The polymerisation zone can be, for example, an autoclave or similar reaction vessel, or a continuous loop reactor, e.g. of the type well-known in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer.

In the process of the present invention employing hydrogen as molecular weight modifier, the quantity of hydrogen employed can vary widely. Generally, the higher the concentration of hydrogen employed, the lower the average molecular weight of the produced polymer. The polymerisation process employing hydrogen gas can be applied to control or reduce the average molecular weight of polymers or copolymers prepared using for example, gas phase, slurry phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of the Formula Z compound employed in the catalyst system). This means that relatively very small quantities of the Formula Z compound are consumed in commercial processes using the process of the present invention. It also means that when the polymerisation process of the present invention is operated under polymer recovery conditions that do not employ a catalyst separation step, thus leaving the supported catalyst, or residues thereof, in the polymer (e.g. as occurs in most commercial slurry and gas phase polymerisation processes), the amount of residual Formula Z compound in the produced polymer can be very small. Experiments carried out with the supported catalyst of the present invention show that, for example, polymerisation of ethylene under slurry polymerisation conditions can provide a particulate polyethylene product containing catalyst so diluted by the produced polyethylene that the concentration of Fe therein falls to, for example, 1 ppm or less wherein "ppm" is defined as parts by weight of Fe per million parts by weight of polymer. Thus polyethylene produced within a polymerisation reactor by the process of the present invention may contain catalyst diluted with the polyethylene to such an extent that the Fe content thereof is, for example, in the range of 1–0.0001 ppm, preferably 1–0.001 ppm.

Suitable monomers for use in the polymerisation process of the present invention are, for example, ethylene, propylene, butene, hexene, methyl methacrylate, methyl acrylate, butyl acrylate, acrylonitrile, vinyl acetate, and styrene. Preferred monomers for homopolymerisation processes are ethylene and propylene. The catalyst is especially useful for copolymerising ethylene with other 1-olefins such as propylene, 1-butene, 1-hexene, 4-methylpentene-1, and octene.

The catalyst of the present invention can also be used for copolymerising ethylene with other monomeric materials, for example, methyl methacrylate, methyl acrylate, butyl acrylate, acrylonitrile, vinyl acetate, and styrene.

The polymerisation conditions employed in the process of the present invention are preferably gas phase or slurry phase. Most preferably the polymerisation is conducted under gas phase fluidised bed conditions.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid is small in relation to the quantity of polymer present in the polymerisation zone. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

In the preferred embodiment of the gas phase polymerisation process of the present invention, the gas phase polymerisation conditions are preferably gas phase fluidised bed polymerisation conditions.

Methods for operating gas phase fluidised bed processes for making polyethylene and ethylene copolymers are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (i.e. the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the, heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and sprayed back into the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

The present invention is illustrated in the following Examples and with reference to FIGS. 1–6 of the accompanying Drawings.

EXAMPLES

In the Examples all manipulations of air/moisture-sensitive materials were performed on a conventional vacuum/inert atmosphere (nitrogen) line using standard Schlenk line techniques, or in an inert atmosphere glove box.

Comparative Example 1

Intermediate A [2,6-diacetylpyridinebis(2,6-diisopropylanil)] was prepared by the reaction of Intermediate B [2,6-diacetylpyridine] and Intermediate C [2,6-diisopropylaniline]. Intermediate A was then reacted with ferrous chloride in butanol to provide the compound of Formula D (see below).

1.1—Preparation of Intermediate A

Using a procedure based on a related preparation (E. C. Alyea and P. H. Merrell, Synth. React. Inorg. Metal-Org. Chem., 1974, 4, 535):-2,6-diisopropylaniline (3.46 ml, 18.4 mmol) was added dropwise to a solution of 2,6-diacetylpyridine (1.50 g, 9.2 mmol) in absolute ethanol (25 ml) [2,6-diisopropylaniline and 2,6-diacetylpyridine were obtained from Aldrich the former of which was freshly distilled before use]. A few drops of glacial acetic acid was added and the solution was refluxed for 48 h. Concentration of the solution to half volume and cooling to −78° C. gave intermediate A as pale yellow crystals (80%). Calcd for $C_{33}H_{43}N_3$: C, 82.3; H, 8.9; N, 8.7; Found: C, 81.9; H, 8.5; 8.7%. FABMS: M+ (481). $^1$H NMR (CDCl$_3$): 8.6–7.9[m, 3H, C$_5$H$_3$N], 7.2–6.9[m, 6H, C$_6$(CHMe$_2$)H$_3$], 2.73[sept, 4H, CHMe$_2$], 2.26[s, 6H, C$_5$H$_3$N(CMeNAr)$_2$] and 1.16[m, 24H, CHMe$_2$]. FABMS is fast atom bombardment mass spectrometry.

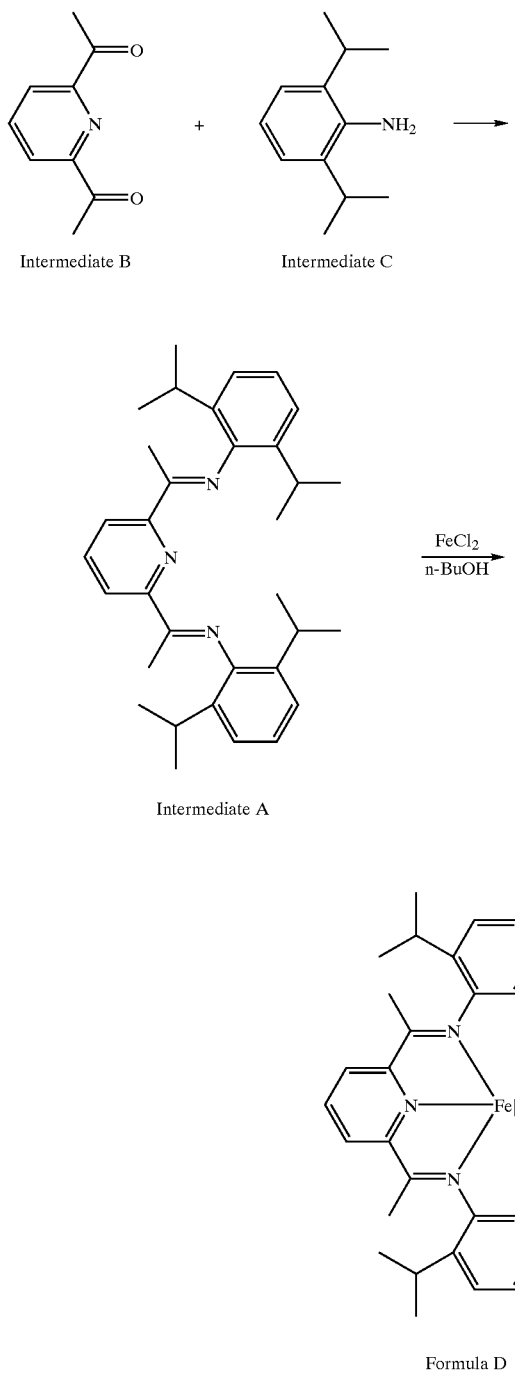

Intermediate B + Intermediate C →

Intermediate A

FeCl₂ / n-BuOH

Formula D

1.2—Preparation of the Formula D Compound

[2,6-diacetylpyridinebis(2,6-diisopropylanil)FeCl₂]

FeCl₂ (0.24 g; 1.89 mmol) was dissolved in hot n-butanol (20 ml) at 80° C. A suspension of 2,6-diacetylpyridinebis (2,6-diisopropylanil) (0.92 g; 1.89 mmol) in n-butanol was added dropwise at 80° C. The reaction mixture turned blue. After stirring at 80° C. for 15 minutes the reaction was allowed to cool down to room temperature. The reaction volume was reduced to a few ml, and petroleum ether (40/60) was added to precipitate the product (a blue powder), which was subsequently washed three times with 10 ml petroleum ether (40/60). The yield was 0.93 g (81%).

Mass spectrum: m/z 607 [M]+, 572 [M−Cl]+, 482 [M−FeCl₂]+.

Analysis—Calculated: for $C_{33}H_{43}N_3FeCl_2$: C, 65.14; H, 7.12; N, 6.91. Found: C, 64.19; H, 6.90; N, 6.70.

Example 9

9.1 Preparation of 2,6-diacetylpyridinebis(2,4,6-trimethylanil)

To a solution of 2,6-diacetylpyridine (0.54 g; 3.31 mmol) in absolute ethanol (20 ml) was added that 2,4,6-trimethyl aniline (1.23 g; 2.5 eq.). After the addition of 2 drops of acetic acid (glacial) the solution was refluxed overnight. Upon cooling to room temperature the product crystallised from ethanol. The product was filtered, washed with cold ethanol and dried in a vacuum oven (50° C.) overnight. The yield was 60% of theoretical.

$^1$H NMR(CDCl₃): 8.50, 7.95, 6.94, (m, 7H, ArH, pyrH), 2.33 (s, 6H, N=CCH₃), 2.28 (s, 6H, CCH₃), 2.05 (s, 12H, CCH₃).

Mass spectrum: m/z 397 $[M]^+$.

9.2—Preparation of 2,6-diacetylpyridinebis(2,4,6-trimethylanil)FeCl₂

FeCl₂ (0.15 g; 1.18 mmol) was dissolved in hot n-butanol (20 ml) at 80° C. A suspension of 2,6-diacetylpyridinebis (2,4,6-trimethylanil) (0.5 g; 1.18 mmol) in n-butanol was added dropwise at 80° C. The reaction mixture turned blue. After stirring at 80° C. for 15 minutes the reaction was allowed to cool down to room temperature. The reaction volume was reduced to a few ml and diethyl ether was added to precipitate the product as a blue powder, which was subsequently washed three times with 10 ml diethyl ether. The yield was 64% of theoretical. Mass spectrum: m/z 523 $[M]^+$, 488 $[M-Cl]^+$, 453 $[M-Cl_2]^+$.

Comparative Examples 14, 15 and 22 to 24

These Comparative Examples are a series of tests wherein ethylene is polymerised under 10 bars ethylene pressure using unsupported catalysts based on 2,6-diacetylpyridinebis(2,6-diisopropylanil)FeCl₂ and 2,6-diacetylpyridinebis(2,4,6-trimethylanil)FeCl₂ under "slurry" polymerisation conditions.

Catalyst Preparation

In Comparative Examples 14 and 15 the complex was 2,6-diacetylpyridinebis(2,6-diisopropylanil)FeCl₂ prepared as described in Comparative Example 1 (Formula D compound), and in Examples 22 to 24 the complex was 2,6-diacetylpyridinebis(2,4,6-trimethylanil)FeCl₂ prepared as described in Example 9.

Catalyst Activation

The iron complex was dissolved in toluene (previously dried over sodium metal) under a nitrogen atmosphere and there was added a solution of activator (cocatalyst) at ambient temperature. The mixture was stirred at room temperature then an aliquot transferred to the injection unit of a polymerisation reactor. The quantities of reagents employed in the catalyst activation are set out in the following Table. All operations were conducted under a nitrogen atmosphere unless specified. "MAO" is methyl aluminoxane (1.78M in toluene supplied by Witco) and was used as purchased. Triisobutylaluminium (Al(iBu)₃) as a 1M solution in toluene was supplied by Aldrich.

TABLE

| Comp Ex. No. | Iron Complex (mg) | [Iron] (μmols) | Cocatalyst type | Cocatalyst (ml) | [Al] mmols | [M]:[Al] | Toluene (ml) | Solution Molarity (M) |
|---|---|---|---|---|---|---|---|---|
| 14 | 3 | 5 | MAO | 2.78 | 5 | 1:1000 | 20 | 0.0025 |
| 15 | 3 | 5 | MAO | 2.78 | 5 | 1:1000 | 20 | 0.0025 |
| 22 | 3 | 6 | MAO | 3.22 | 6 | 1:1000 | 20 | 0.003 |
| 23 | 1.5 | 3 | MAO | 1.61 | 3 | 1:1000 | 10 | 0.003 |
| 24 | 3 | 6 | MAO | 0.32 | 0.3 | 1:100 | 20 | 0.003 |

Polymerisation Tests

The reagents used in the polymerisation tests were Ethylene Grade 3.5 (supplied by Air Products), hexene (supplied by Aldrich) distilled over sodium/nitrogen and triisobutylaluminium (1M in hexanes, supplied by Aldrich).

Polymerisation of Ethylene

A 1 liter reactor was baked under a nitrogen flow for at least 1 hour at >85° C. The reactor was then cooled to 50° C. Isobutane (0.5 liter) and triisobutylaluminium were then added and the reactor was boxed in nitrogen. The alkyl aluminium was allowed to scavenge for poisons in the reactor for at least 1 hour. Ethylene was introduced into the reactor until a predetermined over-pressure was achieved then the catalyst solution was injected under nitrogen. The reactor pressure was maintained constant throughout the polymerisation run by computer controlled addition of additional ethylene. The polymerisation time was 1 hour. Upon termination of the run the reactor contents were isolated, washed with acidified methanol (50 ml HCl/2.5l methanol) and water/ethanol (4:1 v/v) and dried under vacuum, at 40° C., for 16 hours. Data from the polymerisation tests are set out below in the Table.

TABLE

| Comp Ex. No. | [iron] (μmols) | iron/aluminoxane Ratio | $C_2H_4$ Bar | $Al(iBu)_3$ (ml) | polymerisation Temp. (°K.) | polymer (g) | activity (g/mmol M/h/b) | ppm |
|---|---|---|---|---|---|---|---|---|
| 14 | 0.5 | 1:1000 | 10 | 3 | 323 | 26.9 | 5430 | 1.03 |
| 15 | 0.5 | 1:1000 | 10 | 3 | 298 | 45.0 | 9090 | 0.61 |
| 22 | 0.6 | 1:1000 | 10 | 3 | 323 | 63.1 | 11020 | 0.51 |
| 23 | 0.12 | 1:1000 | 10 | 3 | 323 | 55.7 | 48690 | 0.11 |
| 24 | 0.6 | 1:100 | 2 | 2 | 323 | 18.21 | 15150 | 1.84 |

Notes on the Table

"ppm" is defined as parts by weight of iron per million parts by weight of polymer. Molecular weight data of the polymers obtained from the polymerisation tests 14 and 15 are set out in the Table below.

TABLE

| Comp Ex. No. | Mw | Mn | Mpeak | PD |
|---|---|---|---|---|
| 14 | 611000 | 64000 | 246000 | 9.5 |
| 15 | 857000 | 212000 | 451000 | 4.0 |

Comparative Example 26 and Example 27
Gas Phase Polymerisation Tests with Supported Catalysts Comparative Example 26 illustrates the use of a catalyst comprising 2,6-diacetylpyridinebis(2,6-diisopropylanil) $FeCl_2$ supported on silica support material and Example 27 illustrates the use of catalyst comprising 2,6-diacetylpyridinebis(2,4,6-trimethylanil)$FeCl_2$ supported on silica support material.

Comparative Example 26
Preparation of the Supported Catalyst 2,6-Diacetylpyridinebis(2,6-diisopropylanil)$FeCl_2$ was prepared as described in Comparative Example 1. Silica (1.03 g ES70, supplied by Crosfield), which had been heated under flowing nitrogen at 700° C., was placed in a Schlenk tube, and toluene (10 ml) was added. The mixture was heated to 50° C. To a solution of 2,6-diacetylpyridinebis(2,6-diisopropylanil)$FeCl_2$ (0.036 g) in toluene (10 ml) was added methylaluminoxane (5 ml, 1.78M in toluene, supplied by Witco). This mixture was heated at 50° C. and then transferred to the silica/toluene mixture. The silica/MAO/toluene mixture was maintained at 50° C., with regular stirring, for 1 hour before the toluene was removed, at 65° C., under vacuum to yield a free flowing powder.

Example 27
Preparation of the Supported Catalyst 2,6-Diacetylpyridinebis(2,4,6-trimethylanil)$FeCl_2$ was prepared as described in Example 9. Silica (1.38 g ES70, supplied by Crosfield), which had been heated under flowing nitrogen at 700° C., was placed in a Schlenk tube and toluene (10 ml) was added. To a solution of 2,6-diacetylpyridinebis(2,4,6-trimethylanil)$FeCl_2$ (0.041 g) in toluene (10 ml) was added methylaluminoxane (13.2 ml, 1.78M in toluene, supplied by Witco). This mixture was heated at 40° C. for 30 minutes to dissolve as much of the iron complex as possible. The solution was then transferred to the silica/toluene. The silica/MAO/toluene mixture was maintained at 40° C., with regular stirring, for 30 minutes before the toluene was removed, at 40° C., under vacuum to yield a free flowing powder. Analysis of the solid gave 16.9 %w/w Al and 0.144 %w/w Fe.

Polymerisation Tests

Comparative Example 26 and Example 27

The reagents used in the polymerisation tests were: hydrogen Grade 6.0 (supplied by Air Products): ethylene Grade 3.5 (supplied by Air Products): hexene (supplied by Aldrich) distilled over sodium/nitrogen: dried pentane (supplied by Aldrich): methylaluminium (2M in hexanes, supplied by Aldrich): and triisobutylaluminium (1M in hexanes, supplied by Aldrich). A 3 liter reactor was baked out under flowing nitrogen for at least 1 hour at 77–85° C. before powdered sodium chloride (300 g, predried under vacuum, 160° C., >4 hours) was added. The sodium chloride was used as a fluidisable/stirrable start-up charge powder for the gas phase polymerisation. Trimethyl aluminium (3 ml, 2M in hexanes) was added to the reactor and was boxed in nitrogen. The alkyl aluminium was allowed to scavenge for poisons in the reactor for between ½–1 hour before being vented using 4×4 bar nitrogen purges. The gas phase composition to be used for the polymerisation was introduced into the reactor and preheated to 77° C. prior to injection of the catalyst composition. The catalyst (0.18–0.22 g) was injected under nitrogen and the temperature then adjusted to 80° C. The ratio of hexene and/or hydrogen to ethylene during the polymerisation was kept constant by monitoring the gas phase composition by mass spectrometer and adjusting the balance as required. The polymerisation tests were allowed to continue for between 1 to 2 hours before being terminated by purging the reactants from the reactor with nitrogen and reducing the temperature to <30° C. The produced polymer was washed with water to remove the sodium chloride, then with acidified methanol (50 ml HCl/ 2.5 L methanol) and finally with water/ethanol (4:1 v/v). The polymer was dried under vacuum, at 40° C., for 16 hours. Several Runs, using a variety of operating conditions were carried out with each of the catalysts of Examples 26 and 27. All the polymerisation tests were carried out at a polymerisation temperature of 80° C. and at an ethylene pressure of 8 bars. The polymerisation conditions are set out in the following Table

TABLE

| Ex/Run | Iron (% w/w) | MAO/Metal Ratio | other co-catalyst/ (mmols) | $H_2$ (bar) | hexane (bar) | pentane (bar) | Run time (min) | Activity g/mmol M/h/b |
|---|---|---|---|---|---|---|---|---|
| 26.1 | 0.21 | 150 | **** | **** | **** | **** | 75 | 77 |
| 26.2 | 0.21 | 150 | **** | **** | 0.195 | **** | 90 | 77 |
| 26.3 | 0.21 | 150 | TMA /6 | **** | **** | **** | 60 | 149 |
| 26.4 | 0.21 | 150 | TMA /6 | 0.75 | **** | **** | 60 | 318 |
| 27.1 | 0.144 | 300 | **** | **** | **** | **** | 60 | 611 |
| 27.2 | 0.144 | 300 | TMA /6 | 0.5 | **** | **** | 60 | 832 |
| 27.3 | 0.144 | 300 | TMA /6 | 0.5 | 0.2 | **** | 60 | 1054 |
| 27.4 | 0.144 | 300 | TMA /6 | 0.5 | **** | 2.4 | 60 | 1800 |
| 27.5 | 0.144 | 300 | TiBA /3 | **** | **** | **** | 60 | 713 |
| 27.6 | 0.144 | 300 | **** | 3 | **** | **** | 60 | 501 |
| 27.7 | 0.144 | 300 | **** | **** | 0.86 | **** | 60 | 418 |

Figure 5:
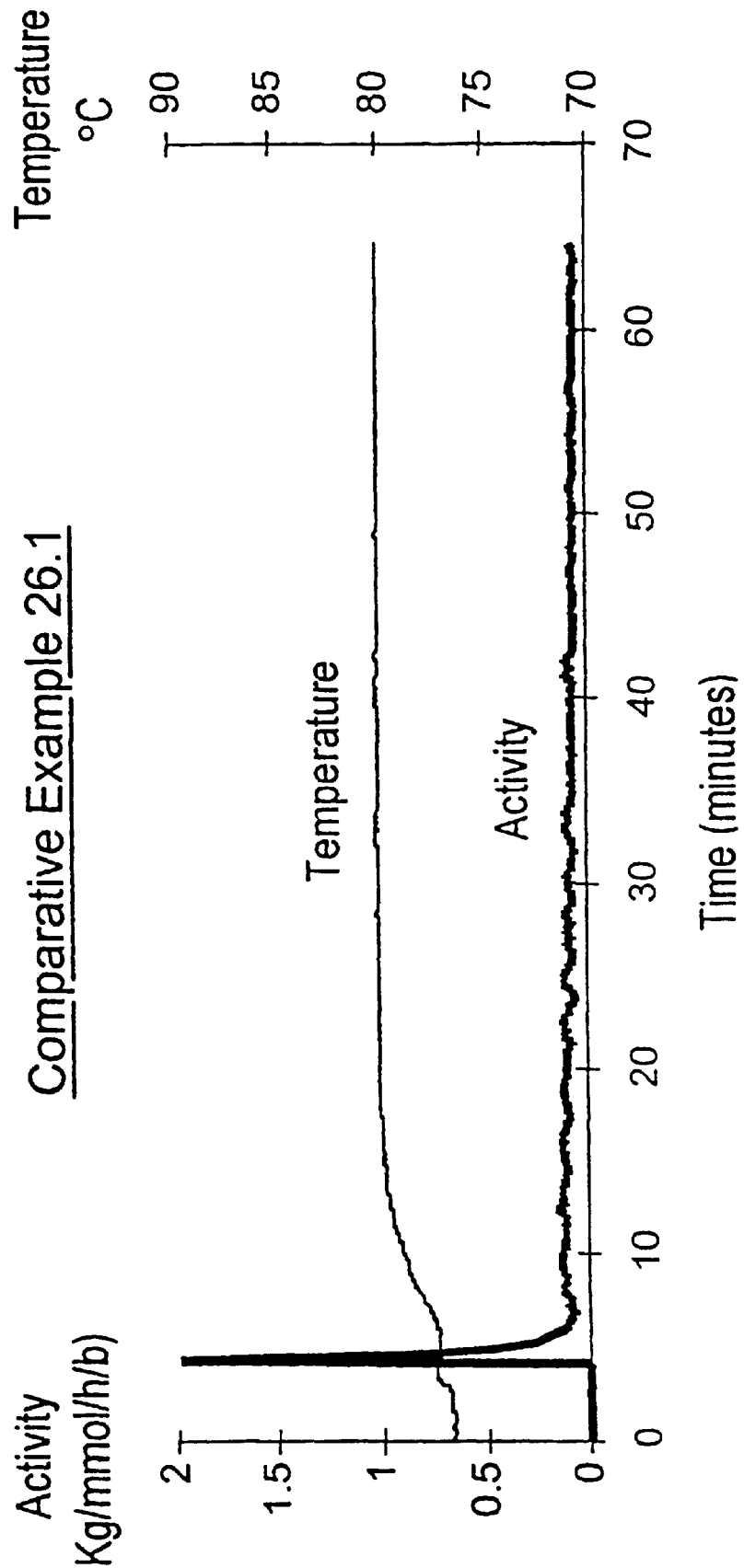

The polymerisation kinetics of Runs 26.1 and 27.1 are illustrated graphically in FIGS. 5 and 6 of the accompanying Drawings. Molecular weight data on the polymer products is set out in the Table below.

| Run | Catalyst | Mw | Mn | Mpeak | Polydispersity |
|---|---|---|---|---|---|
| 26.2 | Ex 26 | 892000 | 106000 | 332000 | 8.4 |
| 26.3 | Ex 26 | 278000 | 8400 | 95000 | 33.0 |
| 26.4 | Ex 26 | 195000 | 7200 | 43000 | 27.0 |
| 27.1 | Ex 27 | 324000 | 9300 | 134000 | 34.6 |
| 27.2 | Ex 27 | 223000 | 18000 | 42000 | 12.3 |
| 27.3 | Ex 27 | 77000 | 6000 | 21000 | 12.8 |

-continued

| Run | Catalyst | Mw | Mn | Mpeak | Polydispersity |
|---|---|---|---|---|---|
| 27.4 | Ex 27 | 154000 | 5700 | 28000 | 26.9 |
| 27.5 | Ex 27 | 207000 | 4800 | 86000 | 43.1 |
| 27.6 | Ex 27 | 69000 | 5400 | 14000 | 12.7 |
| 27.7 | Ex 27 | 127000 | 14000 | 51000 | 9.3 |

The polymer obtained in Example 27.7 contained short chain branching (SCB) corresponding to 1.6 n-butyl branches/1000 C.

Example 32

32.1—Preparation of a Supported Ziegler Catalyst Component

Silica (20 kg), grade ES 70 supplied by Crosfield, which had been dried at 800° C. for 5 hours in flowing nitrogen, was slurried in hexane (110 liters) and hexamethyldisilazane (30 moles), supplied by Fluka, was added with stirring at 50° C. Dry hexane (120 liters) was added with stirring, the solid allowed to settle, the supernatant liquid removed by decantation and further dry hexane (130 liters) was added with stirring. The hexane washing was repeated a further 3 times. Dibutylmagnesium (30 moles), supplied by FMC, was added and stirred for 1 hour at 50° C. Tertiary butyl chloride (60 moles) was added and stirred for 1 hour at 50° C. To this slurry was added an equimolar mixture of titanium tetrachloride (3 moles), and titanium tetra-n-propoxide (3 moles) with stirring at 50° C. for 2 hours, followed by 5 washings with dry hexane (130 liters). The slurry was dried under a flowing nitrogen stream to give a solid, silica supported Ziegler catalyst component.

32.2—Preparation of a Mixed Catalyst Containing a Ziegler Component and 2.6-diacetylpyridinebis(2,4,6-trimethylanil) $FeCl_2$ A solution of methylaluminoxane ("MAO", 10.2 mmol) as a 10% wt solution in toluene, supplied by Witco, was added to a suspension of 2,6-diacetylpyridinebis(2,4,6-trimethylanil)$FeCl_2$ (0.07 mmol in 5 ml dry toluene), prepared as in Example 9, and the mixture shaken for 5 minutes. This solution was then added to 2.0 g of the silica supported Ziegler catalyst prepared above (Example 32.1), the mixture shaken for 2 hours at 20° C. and then the solvent removed under reduced pressure at 20° C. to yield the mixed catalyst as a free flowing powder.

32.3—Polymerisation of Ethylene/hexene Mixture Using the Mixed Catalyst

A 3 liter reactor equipped with a helical stirrer was heated to 95° C. for 1 hour with dry nitrogen flowing through. The temperature was reduced to 50° C. and dry sodium chloride (300 g) was then added with trimethylaluminium (TMA) solution (2 ml of 2 molar TMA in hexane) and the reactor heated at 85° C. for 2 hours. The reactor was purged with nitrogen, cooled to 50° C. and TMA solution (3 ml of 2 molar TMA in hexane) added. The temperature was raised to 77° C. and hydrogen (0.5 bar) and ethylene (8 bar) added prior to the addition of 1-hexene (2.6 ml). Reaction was started by injection into the reactor of the mixed catalyst (0.20 g) prepared above. The temperature was maintained at 80° C. and ethylene added to maintain constant pressure. The gas phase was monitored by a mass spectrometer and hydrogen and 1-hexene added as necessary to maintain constant gas phase concentrations of these components. The polymerisation was carried out for 90 minutes. The polymer was washed with water to remove the sodium chloride, then with acidified methanol (50 ml HCl/2,5 liters methanol) and finally with water/ethanol (4:1 v/v ). The polymer was dried under vacuum, at 40° C. for 16 hours. 111 g of dried polymer was produced. The polymer had a broad molecular weight distribution (as determined by gel permeation chromatography. The polydispersity (Mw/Mn) was 28.5.

Example 33

33.1—Pre-impregnation of Support with Activator Compound

All the following operations were conducted under a nitrogen atmosphere unless stated. Silica (Crosfield grade ES70X) was heated under flowing nitrogen at 250° for 16 hours. A sample of this silica (2.5 g) was placed in a Schlenk tube and had 12.1 ml of 1.78M methylaluminoxane, MAO (supplied by Witco) added to it to form a slurry. The slurry was heated for 4 hours at 50° C. before being left for 10 days at room temperature. The supernatant liquid above the silica was removed and the silica/MAO washed three times with toluene (3×10 ml) at room temperature, removing the supernatant solution each time.

33.2—Supporting the Catalyst (2,6-diacetylpyridinebis(2,4,6 trimethyl anil) iron dichloride (0.101 g) (prepared as described in Example 9) was slurried in toluene (20 ml), at room temperature, and added to the silica/MAO. The mixture was occasionally shaken over a 1 hour period. The supernatant solution was removed and the silica/MAO/Fe complex was washed with toluene until the filtrate was colourless. The solid was dried under vacuum at 50° C.

33.3—Gas Phase Polymerisation of Ethylene

A 3 liter reactor was baked out under flowing nitrogen for at least 1 hour at 77° C. before sodium chloride (300 g, <1 mm diameter particles, predried under vacuum, 160° C., >4 hours) was added. The sodium chloride was employed merely as a standard "charge powder" for the gas phase polymerisation reactor. Trimethyl aluminium (3 ml, 2M in hexanes, supplied by Aldrich) was added to the reactor which was then closed. The alkyl aluminium was allowed to scavenge for poisons in the reactor for ½ hour before being vented by successive pressurising and purging the reactor with 4 bar of nitrogen. Ethylene (Grade 3.5, supplied by Air Products) was added to the reactor to give a pressure of 8 bar, at 77° C., prior to catalyst injection. The supported catalyst (0.215 g) prepared as described in Example 33.2 was injected into the reactor under nitrogen and the temperature then adjusted to 80° C. The polymerisation was allowed to continue for 5 hours before being terminated by purging the ethylene from the reactor, using nitrogen, and reducing the temperature to below 30° C. The polymer was washed with water to remove the sodium chloride, then with acidified methanol (50 ml HCl/2.5 liters methanol) and finally with water/ethanol (4:1 v/v). The polymer was dried under vacuum, at 40° C., for 16 hours. 161 g of dried polymer was produced.

Examples 35 to 38

These illustrate the preparation of supported catalysts in accordance with the present invention and their use in the polymerisation of ethylene under "slurry" polymerisation conditions.

Example 35

35.1—Preparation of 2.6-diacetylpyridinebis(2,4,6 Trimethyl Anil) Iron Dichloride Supported on MAO/silica Silica support material (grade ES70X supplied by Crosfield) was heated under flowing nitrogen at 250° C. for 16 hours. A sample of this silica was placed in a Schlenk tube and 12.1 ml of 1.78M methylaluminoxane ("MAO" supplied by Witco) was added to it to form a slurry. The slurry was heated for 4 hours at 50° C. before being left for 10 days at room temperature. The supernatant liquid above the silica was then removed and the silica/MAO washed 3 times with toluene (10 ml) at room temperature, removing the supernatant solution each time. 2,6-diacetylpyridinebis (2,4,6 trimethyl anil) iron dichloride complex (0.101 g) was slurried in toluene (20 ml), at room temperature, and added to the silica./MAO. The mixture was occasionally shaken over a 1 hour period. The supernatant solution was removed and the produced silica-supported MAO/Fe complex washed with toluene until the initial washings, which were light orange in colour, became clear and free from colour. The produced silica-supported catalyst solid was dried under vacuum at 50° C.

35.2—Polymerisation of Ethylene

A 1 liter reactor was heated under flowing nitrogen (2 liters/min) for 1 hour at 95° C. The reactor was cooled to 40° C. and 500 ml of isobutane added. The temperature of the reactor was raised to 80° C. and ethylene admitted to the reactor to give a partial pressure of 10 bar. The supported catalyst prepared in 35.1 above (0.201 g, slurried in 10 ml of toluene) was injected under nitrogen and the pressure increase in the reactor taken into account during control of the reactor pressure during the polymerisation test. The test was terminated after 1 hour and the polymer dried under vacuum at 40° C. 5.9 g of polymer was recovered. Analysis of the polymer by GPC indicated Mw and Mn to be 124000 and 15000 respectively.

35.3—Polymerisation of Ethylene

A 1 liter reactor was heated under flowing nitrogen for 3 hours at 80° C. The reactor was cooled to less than 30° C. and 500 ml of isobutane added. Trimethyl aluminium (3 ml of 2M in hexanes) was added to the reactor and this was then heated to 80° C. The pressure in the reactor increased to 13.8 bar and then ethylene was admitted to give a total pressure of 23.8 bar. The supported catalyst prepared in 35.1 above (0.201 g of the supported catalyst solid in toluene slurry) was injected into the reactor under nitrogen causing the reactor pressure to increase to 25.4 bar. The catalyst activity was slightly too high for the ethylene inlet flow to keep the pressure constant and this was therefore allowed to fall to 23.2 bar. The ethylene pressure present in the reactor for the majority of the polymerisation was estimated to be 7.8 bar. The test was terminated after 1.75 hours and the polymer washed with methanol/HCl (2.5 liters/50 ml), then water/ethanol (4:1 v/v) and dried under vacuum at 40° C. 166 g of dry polymer was recovered. Analysis of the polymer by GPC indicated Mw and Mn to be 182000 and 11000 respectively.

Example 36

36.1—Preparation of 2,6-diacetylpyridinebis(2,4,6 Trimethyl Anil) Iron Dichloride Supported on MAO/silica A portion (about 1–1.5 g) of the supported catalyst prepared in Example 35.1 was washed with 5×10 ml aliquots of toluene at 100° C. The initial washings had a deep orange colour and this coloration became less with each subsequent washing until the final washing was clear of colour. The solid was dried under vacuum at 100° C. to provide free-flowing solid supported catalyst.

36.2—Polymerisation of Ethylene

A 1 liter reactor was heated under flowing nitrogen for 1 hour at 75° C. Trimethyl aluminium (3 ml of 2M in hexanes) was added to the reactor which was then cooled to 50° C. Isobutane (500 ml) was added to the reactor and the temperature increased to 76° C. The pressure in the reactor increased to 13 bar. Ethylene was admitted to the reactor to give 21 bar total pressure (8 bar ethylene). The supported catalyst prepared in 26.1 above ( 0.11 g in toluene slurry) was injected into the reactor and the pressure increase taken into account during control of the reactor pressure during the test. The temperature was increased to 80° C. After 1 hour a further aliquot of the same catalyst was injected (0.22 g in hexane slurry) and the test continued for a further 3.5 hours. 25 g of polymer was recovered. Analysis of the polymer by GPC indicated Mw and Mn to be 343000 and 35000 respectively.

Example 37

37.1—Preparation of 2,6-diacetylpyridinebis(2,4,6 Trimethyl Anil) Iron Dichloride Supported on MAO/silica Methyl aluminoxane (24 ml of 1.78M in toluene, supplied by Witco) was added to silica (5 g of grade ES70X supplied by Crosfield) which had been heated under flowing nitrogen at 250° C. The silica/MAO was heated at 80° C. for 1 hour before being washed toluene (5×10 ml aliquots). Half of the produced silica/MAO slurry, cooled to room temperature, was used for the next stage of the catalyst preparation (the other half was put aside for use in Example 38). 2,6-Diacetylpyridinebis(2,4,6 trimethyl anil) iron dichloride (73 mg) was slurried in toluene and transferred to the half-portion of silica/MAO/toluene and left to react for 2 hours with occasional mixing. The silica/MAO/Fe complex was washed with toluene (3×10 ml aliquots) at room temperature and then with hexane (2×10 ml aliquots) at room temperature to remove the toluene before finally being washed with hexane at 80° C. (3×10 ml aliquots). The produced supported catalyst solid was dried under vacuum at room temperature. The solid contained 0.107 weight % Fe.

37.2—Polymerisation of Ethylene

A 1 liter reactor was heated under flowing nitrogen for 1 hour at 80° C. The reactor was cooled to less than 30° C. and 500 ml of isobutane added. The reactor was heated to 77° C. and the pressure increased to 13.8 bar. Ethylene was added to give 21.8 bar total pressure (8 bar ethylene). Triisobutyl aluminium (5 ml of 1M in hexanes) was added to the reactor and after 20 minutes the supported catalyst prepared in 37.1 above (0.14 g in hexane slurry) was injected into the reactor and the pressure increase taken into account during control of the reactor pressure during the test. The temperature was increased to 80° C. After 5 hours the polymerisation was terminated. 138 g of polymer was recovered. Analysis of the polymer by GPC indicated Mw and Mn to be 567000 and 53000 respectively. The produced polymer contained 1.02 ppm of Fe arising from the catalyst.

37.3—Polymerisation of Ethylene

A 1 liter reactor was heated under flowing nitrogen for 1 hour at 78° C. The reactor was cooled to less than 30° C. and 500 ml of isobutane added. Triisobutyl aluminium (3 ml of 1M in hexanes) was added to the reactor which was then heated to 78° C. and the pressure increased to 12.1 bar. Ethylene was added to give 32.0 bar total pressure (19.9 bar ethylene). The supported catalyst prepared in 37.1 above (0.0925 g, slurried in hexane) was injected into the reactor and the total pressure was controlled at 31.2 bar. The ethylene pressure during the polymerisation was estimated to be approximately 19.1 bar. Polymerisation was allowed to continue for 80 minutes. 181 g of polymer was recovered. Analysis of the polymer by GPC indicated Mw and Mn to be 595000 and 44000 respectively. The polymer contained 0.51 ppm of Fe arising from the catalyst.

37.4—Polymerisation of Ethylene

A 1 liter reactor was heated under flowing nitrogen for 1 hour at 80° C. before being cooled to less than 30° C. Triisobutyl aluminium (3 ml of 1M in hexanes) was added to the reactor followed by 500 ml of isobutane. The reactor was heated to 78° C. and the pressure increased to 13.5 bar. Ethylene was added to give 17.6 bar total pressure (4.1 bar ethylene). The supported catalyst prepared in 37.1 above (0.15 g, slurried in hexane) was injected into the reactor. The ethylene pressure during the polymerisation was estimated to be approximately 4.7 bar. Polymerisation was allowed to continue for 80 minutes. 21 g of polymer was recovered. Analysis of the polymer by GPC indicated Mw and Mn to be 347000 and 26000 respectively.

Example 39

Polymerisation of Ethylene in Slurry Phase Using a Supported Catalyst

A series of polymerisation tests was carried out using a catalyst based on a supported 2,6-diacetylpyridinebis(2,4,6 trimethyl anil) iron dichloride.

Example 39.1

A 1 liter reactor was heated under flowing nitrogen for 1 hour at 80° C. before being cooled to 30° C. Isobutane (500 ml) followed by triisobutyl aluminium (3 ml of 1M in hexanes) was added to the reactor. The reactor was heated to 78° C. and the pressure increased to 13.2 bar. Ethylene was added to give 26.2 bar total pressure. The catalyst of Example 37.1 (0.097 g, slurried in hexane) was injected into the reactor. The reactor pressure was controlled at 26.0 bar during the test (ethylene pressure estimated to be approximately 12.8 bar) and the temperature adjusted to 80° C. Polymerisation was allowed to continue for 60 minutes. 78 g of polymer was recovered. Analysis of the polymer by GPC indicated Mw and Mn to be 528000 and 40000 respectively.

Example 39.2

A 1 liter reactor was heated under flowing nitrogen for 1 hour at 80° C. before being cooled to 30° C. Isobutane (500 ml) followed by triisobutyl aluminium (3 ml of 1M in hexanes) was added to the reactor. The reactor was heated to 78° C. and the pressure increased to 13.4 bar. Ethylene was added to give 21.2 bar total pressure. The catalyst of Example 37.1 (0.124 g, slurried in hexane) was injected into the reactor. The ethylene pressure was estimated to be approximately 8.1 bar during the polymerisation and the temperature adjusted to 80° C. Polymerisation was allowed to continue for 60 minutes. 47 g of polymer was recovered. Analysis of the polymer by GPC indicated Mw and Mn to be 376000 and 40000 respectively. The polymerisation kinetics of Example 39.2 is illustrated graphically in FIG. 4 of the accompanying Drawings.

Example 39.3

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 13.0 bar. Ethylene was added to give 26.0 bar total pressure. The catalyst of Example 37.1 (0.0966 g, slurried in hexane and 0.25 ml of NN dimethylaniline for 20 minutes) was injected into the reactor. The pressure in the reactor was allowed to fall to 22.5 bar to reduce the activity of the catalyst. The ethylene pressure in the reactor during the majority of the polymerisation was estimated to be 9.0 bar. Polymerisation was allowed to continue for 60 minutes. 88 g of polymer was recovered. Analysis of the polymer by GPC indicated Mw and Mn to be 430000 and 35000 respectively.

Example 39.4

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 12.7 bar. Ethylene was added to give 14.7 bar total pressure. The catalyst of Example 37.1(0.104 g, slurried in hexane) was injected into the reactor. The ethylene pressure during the polymerisation was estimated to be approximately 2.2 bar. Polymerisation was allowed to continue for 60 minutes. 4.8 g of polymer was recovered. Analysis of the polymer by GPC indicated Mw and Mn to be 340000 and 36000 respectively.

Example 41

This Example shows the use of a combination of a metallocene-type catalyst with the catalyst of the present invention for polymerising ethylene under slurry conditions.
41.1—Preparation of a Supported Metallocene Catalyst To silica (Crosfield grade ES70, previously calcined at 200° C. in flowing $N_2$ for 5 hrs) was added a toluene solution of methylaluminoxane (MAO) containing dissolved bis(n-butylcyclopentadienyl)$ZrCl_2$. The amounts used were 2.5 mmol MAO per gram of silica and 0.05 mmol metallocene per gram silica. The resulting slurry was stirred gently for at least 1 hour before being dried under reduced pressure to give a free flowing powder.
41.2—Preparation of the Combined Metallocene/Fe-complex Catalyst The supported metallocene catalyst (2.5 g) prepared as described in step 41.1 above was placed in a Schlenk tube and a slurry of 2,6-diacetylpyridinebis(2,4,6 trimethyl anil) iron dichloride (73 mg) in hexane (10 ml) was added thereto at ambient temperature. The mixture was heated to 80° C. and left for 90 minutes with occasional shaking to maintain a well-mixed solution. There was no coloration evident in the supernatant solution above the solid. The produced catalyst was dried at 80° C. under vacuum to leave a dry free flowing powder.
41.3—Polymerisation of Ethylene A 1 liter reactor was heated under flowing nitrogen for 1 hour at 80° C. before being cooled to 30° C. Triisobutyl aluminium (3 ml of 1M in hexanes) was added to thereactor followed by 500 ml of isobutane. The reactor was heated to 77° C. and the pressure increased to 12.9 bar. Ethylene was added to give 20.9 bar total pressure. The catalyst (0.100 g, slurried in hexane) prepared as described in 41.2 above was injected into the reactor. The ethylene pressure during the polymerisation was estimated to be approximately 8 bar. Polymerisation was allowed to continue for 60 minutes. 96 g of polymer was recovered. Analysis of the polymer by GPC indicated Mw and Mn to be 471000 and 30000 respectively.

Comparative Test 41.4

This shows the polymerisation of ethylene using only the supported metallocene catalyst described in step 41.1. A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 75° C. and the pressure increased to 12.7 bar. Ethylene was added to give 20.7 bar total pressure. The supported metallocene catalyst (0.094 g, slurried in hexane) prepared in step 41.1 above was injected into the reactor. The ethylene pressure during the polymerisation was estimated to be approximately 8 bar. Polymerisation was allowed to continue for 60 minutes. 49 g of polymer was recovered. Analysis of the polymer by GPC indicated Mw and Mn to be 142000 and 53000 respectively.

Example 42

Gas Phase Polymerisation

This Example shows the use of a combination of a metallocene-type catalyst with a catalyst based on an iron complex of the present invention for polymerising ethylene under gas phase polymerisation conditions. A 3 liter reactor was baked out under flowing nitrogen for least 1 hour at 78° C. before being cooled to 30° C. Powdery sodium chloride (300 g) charge powder having an average particle diameter of less than 1 millimeter 1 mm and having been predried under vacuum at 160° C. for more than 4 hours, was added followed by trimethyl aluminium (3 ml, 2M in hexanes, supplied by Aldrich). The reactor was then closed and heated to 78° C. The alkyl aluminium was allowed to scavenge any poisons present in the reactor for 90 minutes. The reactor was then purged, four times, by pressurising to 4 bars with nitrogen, and then venting. Hydrogen was added to the reactor give 0.08 bar pressure followed by ethylene (8 bar). The catalyst (0.20 g,) as prepared in step 41.3 above was injected under nitrogen and the temperature then adjusted to 80° C. The polymerisation was allowed to continue for 60 minutes before being terminated by purging the ethylene from the reactor, using nitrogen, and reducing the temperature to below 30° C. The polymer was washed with water to remove the sodium chloride, then with acidified methanol (50 ml HCl/2.5 liters methanol) and finally with water/ ethanol (4:1 v/v). The polymer was dried under vacuum, at 40° C., for 16 hours. 64 g of dried polymer was produced. The GPC (gel permeation chromatogram) was run for the polymer product. The produced GPC curve was distinctly bimodal with Mw=253000 and a polydispersity of 64.9.

Comparative Examples 43 and 44

These show polymerisation of ethylene under "slurry" conditions using unsupported catalysts. Comparative Example 43 shows the use of a catalyst based on 2,6-diacetylpyridinebis(2,6-diisopropylanil)$FeCl_2$ and Comparative Example 44 shows the use of a catalyst based on 2,6-diacetylpyridinebis(2,4,6-trimethylail)$FeCl_2$, both catalysts being activated with MAO. The kinetics of the polymerisation tests ae shown in FIGS. 1 and 2 of the attached Drawings.
Catalyst Preparation and Activation The iron complex was dissolved in toluene (previously dried over sodium metal under a nitrogen atmosphere and there was added a solution of methyl aluminoxane (1.78M in toluene, supplied by Witco) at ambient temperature. The mixture was stirred at room temperature then an aliquot transferred to the injection unit of the polymerisation reactor. The quantities of reagents employed in the catalyst activation are set out in the following Table. All operations were conducted under a nitrogen atmosphere unless specified.

| Comp Ex. No. | Iron Complex (mg) | [Iron] (μmols) | Cocatalyst type | (ml) | [Al] mmols | [M]:[Al] | Toluene (ml) | Solution Molarity (M) |
|---|---|---|---|---|---|---|---|---|
| 43 | 3 | 5 | MAO | 2.78 | 5 | 1:1000 | 20 | 0.0025 |
| 44 | 3 | 6 | MAO | 0.32 | 0.6 | 1:100 | 20 | 0.003 |

Polymerisation Tests

The reagents used in the polymerisation tests were Ethylene Grade 3.5 (supplied by Air Products and triisobutylaluminium (1M in hexanes, supplied by Aldrich).
Polymerisation of Ethylene A 1 liter reactor was baked out under a nitrogen flow for at least 1 hour at >85° C. The reactor was then cooled to 50° C. Isobutane (0.5 liter) and triisobutylaluminium were then added and the reactor was boxed in nitrogen. The alkyl aluminium was allowed to scavenge for poisons in the reactor for at least 1 hour. Ethylene was introduced into the reactor until a 2 bar over-pressure was achieved then the catalyst solution was injected under nitrogen. The reactor pressure was maintained constant throughout the polymerisation run by computer controlled addition of additional ethylene. The polymerisation time was 1 hour. Upon termination of the run the reactor contents were isolated, washed with acidified methanol (50 ml HCl/2.5l methanol) and water/ethanol (4:1 v/v) and dried under vacuum, at 40° C., for 16 hours. Data from the polymerisation tests are set out below in the Table.

| Comp Ex. No. | [Iron] (μmols) | Iron/aluminoxane Ratio | Al(iBu)$_3$ (ml) | polym. Temp. (° K.) | polymer (g) | activity (g/mmol M/h/b) |
|---|---|---|---|---|---|---|
| 43 | 0.6 | 1:1000 | 3 | 323 | 10.7 | 9010 |
| 44 | 0.6 | 1:100 | 3 | 323 | 18.2 | 15900 |

Comparative Example 45

Figure 3:
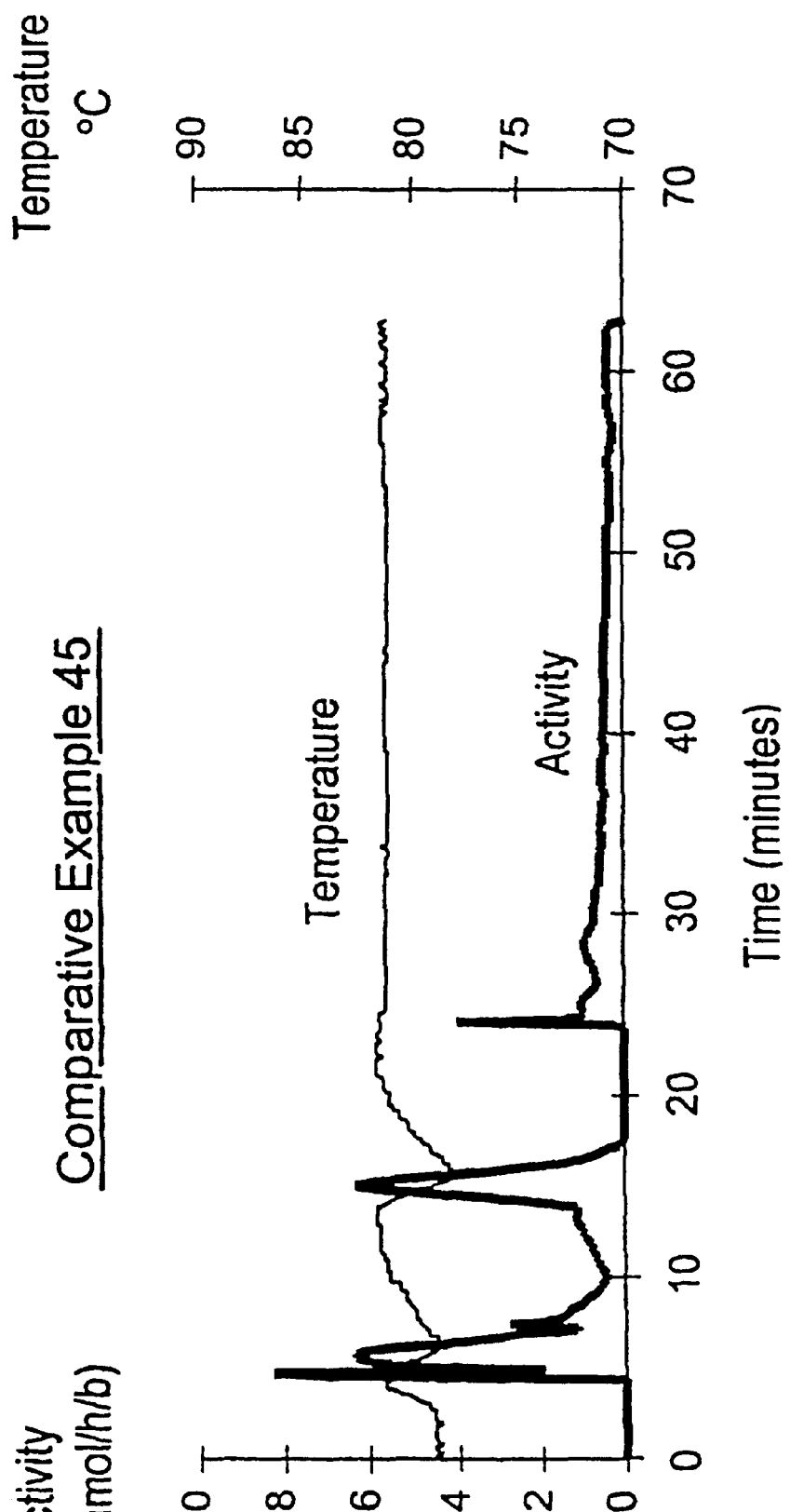

This shows polymerisation of ethylene under slurry conditions using a supported catalysts based on 2,6-diacetylpyridinebis(2,6-diisopropylanil)FeCl$_2$ supported on silica. Both catalysts were activated with MAO. The kinetics of the polymerisation test is shown in FIG. 3 of the attached Drawings.

45.1—Preparation of 2,6-diacetylpyridinebis(2.6 diisopropylanil) Iron Dicholoride Supported on MAO/silica Methyl aluminoxane (62 ml of 1.78M in toluene, supplied by Witco) was added to silica (25 g of grade ES70X supplied by Crosfield) which had been heated under flowing nitrogen at 250° C. The silica/MAO was heated at 80° C. for 1 hour, then dried under vacuum 2.0 g of this treated silica was added to a sample of 2,6-diacetylpyridinebis(2,6 diisopropylanil) iron dichloride (31 mg). The solids were mixed, then toluene (5 ml) was added to form an orange/brown slurry. After mixing for 30 minutes, the solvent was removed at 80° C. under vacuum to yield a free-flowing tan powder.

45.2—Polymerisation of Ethylene

A 1 liter reactor was heated under flowing nitrogen for 1 hour at 80° C. The reactor was cooled to less than 30° C. and 500 ml of isobutane added. The reactor was heated to 80° C. and the pressure increased to 14.6 bar. Ethylene was added to give 22.6 bar total pressure (8 bar ethylene). Triisobutyl aluminium (3 ml of 1M in hexanes) was added to the reactor and after 20 minutes the supported catalyst prepared in 37.1 above (0.10 g) was injected into the reactor and the pressure increase taken into account during control of the reactor pressure during the test. After 1 hours the polymerisation was terminated. 16 g of polymer was recovered. Analysis of the polymer by GPC indicated Mw and Mn to be 458000 and 75000 respectively. The polymerisation kinetics of Example 45 is illustrated graphically in FIG. 3 of the accompanying Drawings.

Example 46

Polymerisation of Ethylene in Slurry Phase Using a Supported Catalyst

A series of polymerisation tests was carried out using a catalyst based on a supported 2,6-diacetylpyridinebis(2,4,6 trimethyl anil) iron dichloride.

Example 46.1

A 1 liter reactor was heated under flowing nitrogen for 1 hour at 80° C. before being cooled to 30° C. Isobutane (500 ml) followed by triisobutyl aluminium (3 ml of 1M in hexanes) was added to the reactor. The reactor was heated to 78° C. and the pressure increased to 13.2 bar. Ethylene was added to give 26.2 bar total pressure. The catalyst of Example 37.1 (0.097 g, slurried in hexane) was injected into the reactor. The reactor pressure was controlled at 26.0 bar during the test (ethylene pressure estimated to be approximately 12.8 bar) and the temperature adjusted to 80° C. Polymerisation was allowed to continue for 60 minutes. 78 g of polymer was recovered. Analysis of the polymer by GPC indicated Mw and Mn to be 528000 and 40000 respectively.

Example 46.2

A 1 liter reactor was heated under flowing nitrogen for 1 hour at 80° C. before being cooled to 30° C. Isobutane (500 ml) followed by triisobutyl aluminium (3 ml of 1M in hexanes) was added to the reactor. The reactor was heated to 78° C. and the pressure increased to 13.4 bar. Ethylene was added to give 21.2 bar total pressure. The catalyst of Example 37.1 (0.124 g, slurried in hexane) was injected into the reactor. The ethylene pressure was estimated to be approximately 8.1 bar during the polymerisation and the temperature adjusted to 80° C. Polymerisation was allowed to continue for 60 minutes. 47 g of polymer was recovered. Analysis of the polymer by GPC indicated Mw and Mn to be 376000 and 40000 respectively.

Example 46.3

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 13.0 bar. Ethylene was added to give 26.0 bar total pressure. The catalyst of Example 37.1 (0.0966 g, slurried in hexane and 0.25 ml of NN dimethylaniline for 20 minutes) was injected into the reactor. The pressure in the reactor was allowed to fall to 22.5 bar to reduce the activity of the catalyst. The ethylene pressure in the reactor during the majority of the polymerisation was estimated to be 9.0 bar. Polymerisation was allowed to continue for 60 minutes. 88 g of polymer was recovered. Analysis of the polymer by GPC indicated Mw and Mn to be 430000 and 35000 respectively.

Example 46.4

A 1 liter reactor was heated under flowing nitrogen for 1 hour at 80° C. before being cooled to 30° C. Triisobutyl aluminium (3 ml of 1M in hexanes) was added to the reactor followed by 500 ml of isobutane. The reactor was heated to 78° C. and the pressure increased to 12.7 bar. Ethylene was added to give 14.7 bar total pressure. The catalyst of Example 37.1(0.104 g, slurried in hexane) was injected into the reactor. The ethylene pressure during the polymerisation was estimated to be approximately 2.2 bar. Polymerisation was allowed to continue for 60 minutes. 4.8 g of polymer was recovered. Analysis of the polymer by GPC indicated Mw and Mn to be 340000 and 36000 respectively.

Example 47

Slurry Loop Polymerisation 47.1—Preparation of 2,6-diacetylpyridinebis(2,4,6 Trimethyl Anil) Iron Dichloride Supported on MAO/silica All operations were conducted under nitrogen unless specified. Silica (256.62 g of grade ES70X supplied by Crosfield), calcined at 200° C. under flowing nitrogen, was placed in a 2 L round bottomed flask. Toluene (900 ml) was added to the silica followed by methyl aluminoxane (441 ml, 1.5M in toluene supplied by Witco). The MAO was allowed to react with the silica at room temperature for 10 minutes at which point the temperature was raised to 80° C. and the slurry was mixed occasionally by manually shaking the flask. The temperature was maintained between 80–100° C. for a period of 2 hours.

2,6-diacetylpyridinebis(2,4,6 trimethyl anil) iron dichloride prepared as in Example 9 above (3.48 g) was slurried in toluene (50 ml) and added to the MAO/silica slurry at 80° C. A further aliquot of toluene (20 ml) was used to ensure that all of the Fe complex was transferred to the MAO/silica. The Fe/MAO/silica was then heated at 80° C., with occasional shaking, for 1.5 hours and the solid allowed to settle. The clear supernatant solution was decanted from the flask and the catalyst partially dried under vacuum at 80° C. for 30 minutes and then left at room temperature for 16 hours. Drying of the catalyst was then continued, at 80° C. under vacuum for a further 5 hours, until a dry free flowing powder resulted and no more solvent could be detected coming off the support.

47.2—Pilot Scale Polymerisations (Slurry)

A 93 liter Phillips continuous polymerisation loop reactor was used for the polymerisations. Ethylene, isobutane diluent, hydrogen and the catalyst prepared in Example 1.3 above were metered into the reactor to maintain the reaction conditions as detailed in the Table below. The reactor was operated at a polyethylene throughput of approximately 7.5 kg/hour. Polymer molecular weight was controlled by variation of hydrogen addition rate.

| Pilot scale conditions | |
|---|---|
| Temperature (° C.) | 90 |
| Pressure (psig) | 600 |
| Production rate (kg/hr) | 7.4 |
| Ethylene (vol %) | 16.1 |
| Isobutane (litres/hour) | 24 |
| Hydrogen conc. (vol %) | 0.13 |
| Residence time (hours) | 1.6 |
| Catalyst Productivity (g/g) | 5310 |
| Compounded product: | |
| $M_n$ | 34200 |
| $M_w$ | 255500 |
| HLMI (21.6 kg: g/10 mins) | 4.7 |
| Density (kg/m$^3$) | 959.9 |

Figure 2:
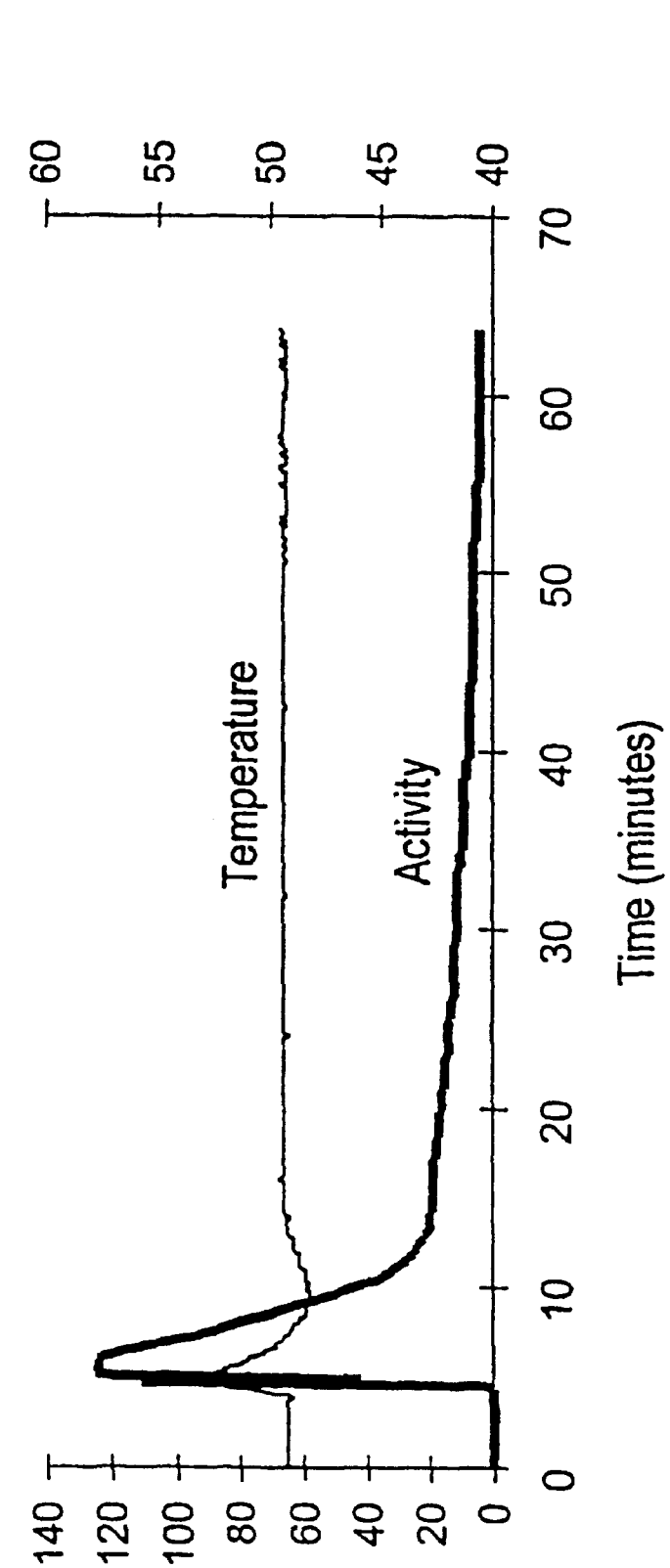

FIGS. 1 and 2 of the Drawings show the kinetic profiles of ethylene polymerisation under "slurry" conditions using unsupported catalysts comprising 2,6-diacetylpyridinebis(2,6-diisopropylanil)FeCl$_2$ (FIG. 1) and 2,6-diacetylpyridinebis(2,4,6-trimethylanil)FeCl$_2$ (FIG. 2) both catalysts being activated with MAO. It is clear from these kinetic profiles that both catalysts are highly active initially, but that activity falls off rapidly as polymerisation proceeds.

Figure 4:
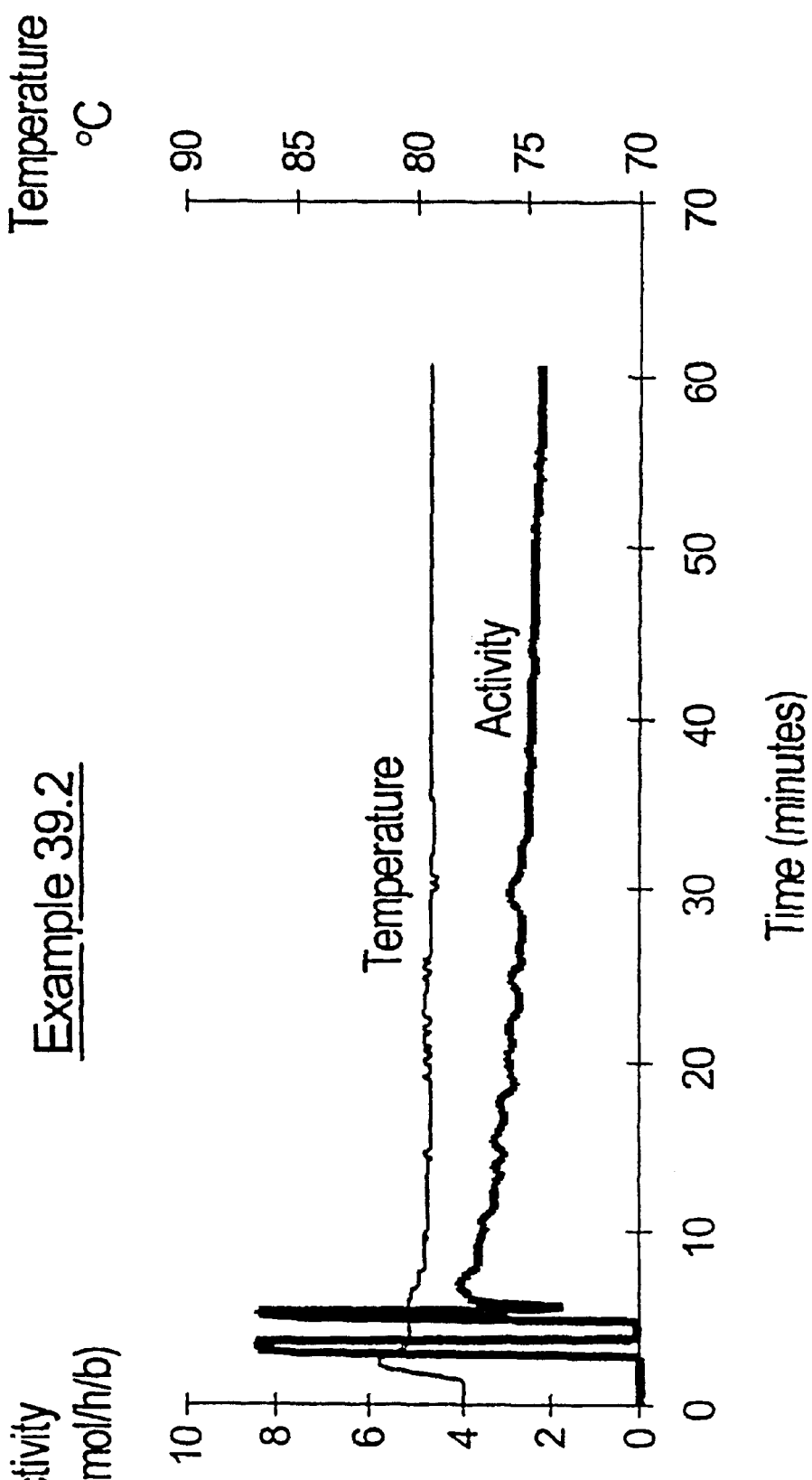

FIGS. 3 and 4 of the Drawings show the kinetic profiles of ethylene polymerisation under "slurry" conditions using silica supported catalysts comprising 2,6-diacetylpyridinebis(2,6-diisopropylanil)FeCl$_2$ (FIG. 3—Comparison) and 2,6-diacetylpyridinebis(2,4,6-trimethylanil)FeCl$_2$ (FIG. 4—Invention) both catalysts being activated with MAO. It can be seen that the activity of the catalyst of the present invention is relatively high at the commencement of the polymerisation, and only gradually diminishes as the polymerisation proceeds. On the other hand, in the Comparative Example (FIG. 3) the initial high activity rapidly reduced early in the course of the polymerisation.

FIGS. 5 and 6 of the Drawings show the kinetic profiles of ethylene polymerisation under "gas phase" conditions using silica supported catalysts comprising 2,6-diacetylpyridinebis(2,6-diisopropylanil)FeCl$_2$ (FIG. 5—Comparison) and 2,6-diacetylpyridinebis(2,4,6-trimethylanil)FeCl$_2$ (FIG. 6—Invention) both catalysts being activated with MAO. In the Comparative Example the initial high activity falls away very rapidly to a comparatively low level of activity. In FIG. 6, it can be seen that the catalyst of the present invention provides relatively high initial activity, and exhibits almost constant activity for the duration of the polymerisation test.

What is claimed is:

1. A polymerization catalyst comprising (1) a nitrogen-containing iron compound having the following Formula Z,

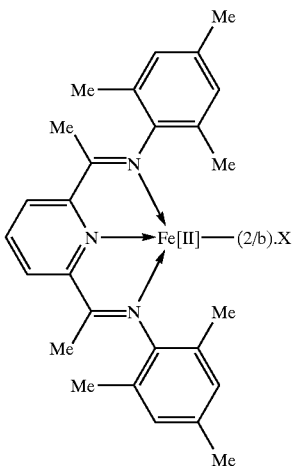

Formula Z

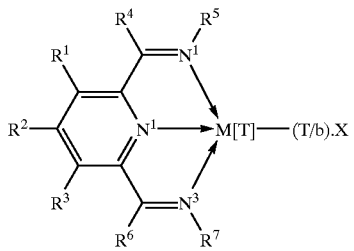

Formula B and (2) an activating quantity of an activator compound selected from the group consisting of organoaluminium compounds and hydrocarbylboron compounds wherein X represents an atom or group covalently or ionically bonded to the Fe and b is the valency of the atom or group X, and the catalyst is supported on (3) a solid particulate support material.

2. The catalyst of claim 1, wherein the atom or group represented by X is selected from the group consisting of halide, sulphate, nitrate, thiolate, thiocarboxylate, $BF_4^-$, $BF_6^-$, hydride, hydrocarbyloxide, carboxylate, hydrocarbyl, substituted hydrocarbyl and heterohydrocarbyl.

3. The catalyst of claim 1, wherein the atom or group represented by X is selected from the group consisting of chloride, bromide, iodide, methyl, ethyl, proply, butyl, octyl, decyl, phenyl, benzyl, methoxide, ethoxide, isopropoxide, tosylate, triflate, formate, acetate, phenoxide and benzoate.

4. The catalyst of claim 1, wherein the compound of Formula Z is 2,6-diacetylpyridinebis(2,4,6 trimethyl anil) $FeCl_2$.

5. The catalyst of claim 1, wherein the activator compound is an alkylalumoxane.

6. The catalyst of claim 5, wherein the alkylalumoxane is methylalumoxane.

7. The catalyst of claim 1, wherein the activator compound is dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+$ $(OEt_2)[(bis-3,5-trifluoromethyl)phenyl]borate$, trityltetra(pentafluorophenyl)borate or tris(pentafluorophenyl) boron.

8. The catalyst of claim 1, wherein the solid particulate support material is an inorganic oxide, hydroxide or salt.

9. The catalyst of claim 8, wherein the solid particulate support is silica, alumina, silica-alumina, zirconia, magnesium oxide, magnesium chloride, pumice, talc, kieselguhr, calcium carbonate, calcium sulphate, an organic polymer or an organic prepolymer.

10. The catalyst of claim 1, wherein the activator compound is methylalumoxane and the solid particular support material is silica, silica-alumina, or alumina.

11. The catalyst of claim 1, which additionally comprises as a further catalyst a Ziegler Natta catalyst supported on a magnesium halide, a Phillips supported catalyst, a supported metallocene catalyst, or a compound having the general Formula B.

wherein

M is Fe[II], Fe[III], Co[I], Co[II], Co[III], Ru[II], Ru[III] or Ru[IV]; Mn[I], Mn[II], Mn[III], or Mn[IV], X represents an atom or group covalently or ionically bonded to the transition metal M; T is the oxidation state of the transition metal M and b is the valency of the atom or group X; $R^1$, $R^2$, $R^3$, $R^4$, and $R^6$ are independently selected from the group consisting of hydrogen, halogen, hydrocarbyl, substituted hydrocarbyl, heterohydrocarbyl and substituted heterohydrocarbyl and such that (1):

when M is Fe, Co or Ru, $R^5$ and $R^7$ are independently selected from the group consisting of hydrogen, halogen, hydrocarbyl, substituted hydrocarbyl, heterohydrocarbyl and substituted heterohydrocarbyl; and when any two or more of $R^1$–$R^7$ are hydrocarbyl, substituted hydrocarbyl, heterohydrocarbyl or substituted heterohydrocarbyl, said two or more of $R^1$–$R^7$ can be linked to form one or more cyclic substituents;

or such that (2):

when M is Fe, Co, Mn or Ru, then $R^5$ is presented by the group "P" and $R^7$ is represented by the group "Q" as follows:

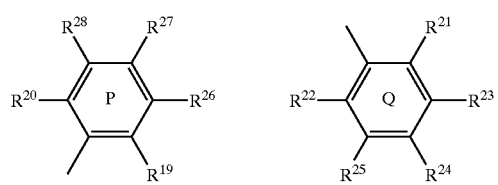

wherein $R^{19}$ to $R^{28}$ are independently selected from the group consisting of hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more of $R^1$ to $R^4$, $R^6$ and $R^{19}$ to $R^{28}$ can be linked to form one or more cyclic substituents; with the proviso that at least one of $R^{19}$, $R^{20}$, $R^{21}$ and $R^{22}$ is hydrocarbyl, substituted hydrocarbyl, heterohydrocarbyl or substituted heterohydrocarbyl when neither of ring systems P and Q forms part of a polyaromatic fused-ring system, or such that (3)

when M is Fe, Co, Mn or Ru, then $R^5$ is a group having the formula $—NR^{29}R^{30}$ and $R^7$ is a group having the formula $—NR^{31}R^{32}$, wherein $R^{29}$ to $R^{32}$ are independently selected from the group consisting of hydrogen, halogen, hydrocarbyl, substituted hydrocarbyl, heterohydrocarbyl or substituted heterohydrocarbyl; when any two or more of $R^1$ to $R^4$, $R^6$ and $R^{29}$ to $R^{32}$ are hydrocarbyl, substituted hydrocarbyl, heterohydrocarbyl or substituted heterohydrocarbyl, said two or more of $R^1$ to $R^4$, $R^6$ and $R^{29}$ to $R^{32}$ can be linked to form one or more cyclic substituents; provided that said compound of Formula B is different from said compound of Formula Z.

12. The catalyst of claim 11, wherein said further catalyst forms part of the support material.

13. The catalyst of claim 1, further comprising (4) a neutral Lewis base.

14. The catalyst of claim 13, wherein the neutral Lewis base is a tertiary amine or an aromatic ester.

15. The catalyst of claim 1, wherein the particle size of the support material is in the range 5 to 500 microns.

16. The catalyst of claim 15, wherein the particular size is in the range of 20 to 200 microns.

17. The catalyst of claim 1, wherein the surface area of the support material is in the range of 5 to 100 $m^2$ per gram.

18. The catalyst of claim 17, wherein the surface area is in the range of 50 to 500 $m^2$ per gram.

19. The catalyst of claim 1, which contains not more than 30 weight % of liquid diluent.

20. The catalyst of claim 19, which contains not more than 10 weight % of liquid diluent.

21. The catalyst of claim 20, which contains not more than 1 weight % of liquid diluent.

22. A process for making a catalyst as defined in claim 1, comprising dissolving or suspending compounds (1) and (2) in a suitable diluent or solvent, slurrying them with the support material (3), and optionally then separating the support material thus impregnated with catalyst from the solvent or diluent.

23. A process for the polymerization or copolymerization of 1-olefins, comprising contacting a monomeric olefin or monomeric olefins under polymerization conditions with a polymerization catalyst as defined in claim 1.

24. The process of claim 23, wherein the polymerization is conducted in the presence of hydrogen as a molecular weight modifier.

25. The process of claim 23, wherein the polymerization is the polymerization of ethylene or propylene.

26. The process of claim 23, wherein ethylene is copolymerized with another 1-olefin selected from the group consisting of propylene, 1-butene, 1-hexene, 4-methylpentene-1 and octane.

27. the process of claim 23, wherein the polymerization temperature is in the range 50 to 120° C. and the pressure is in the range 10 to 50 bar.

28. The process of claim 23, wherein the polymerization conditions are solution phase, slurry phase or gas phase.

29. The process of claim 23, wherein the polymerization is conducted under gas phase fluidized bed conditions.

30. The process of claim 23, wherein the polymerization is conducted in slurry phase in an autoclave or continuous loop reactor.

31. Particular polyethylene containing a catalyst as defined in claim 1, wherein the Fe concentration is 1 ppm or less.

32. Particulate polyethylene according to claim 31, wherein the Fe concentration is from 1 ppm to 0.0001 ppm.

* * * * *